United States Patent [19]

Sendax

[11] Patent Number: 4,975,059
[45] Date of Patent: Dec. 4, 1990

[54] CAST DENTAL IMPLANT ABUTMENT

[75] Inventor: Victor I. Sendax, New York, N.Y.

[73] Assignee: Sendax Dental Implant Magnetics, Inc., New York, N.Y.

[21] Appl. No.: 300,671

[22] Filed: Jan. 23, 1989

[51] Int. Cl.$^5$ .............................................. A61C 8/00
[52] U.S. Cl. ..................................... 433/173; 433/189
[58] Field of Search ............... 433/173, 220, 221, 174, 433/175, 176, 221.1, 219, 218, 225, 189; 128/92 YG

[56] References Cited

U.S. PATENT DOCUMENTS

| | | | |
|---|---|---|---|
| 2,745,180 | 5/1956 | Kiernan | 433/175 |
| 2,857,670 | 10/1958 | Kiernan | 433/175 |
| 3,514,858 | 6/1970 | Silverman | 433/174 |
| 3,589,011 | 6/1971 | Sneer | 433/174 |
| 3,955,280 | 5/1976 | Sneer | 433/169 |
| 4,011,602 | 3/1977 | Rybicki et al. | 623/16 |
| 4,146,936 | 4/1979 | Aoyagi et al. | 433/173 |
| 4,199,864 | 4/1980 | Ashman | 433/175 |
| 4,209,905 | 7/1980 | Gillings | 433/189 |
| 4,302,189 | 11/1981 | Gillings | 433/189 |
| 4,324,550 | 4/1982 | Reuther et al. | 433/174 |
| 4,416,629 | 11/1983 | Mozsary et al. | 433/174 |
| 4,431,419 | 2/1984 | Portnoy | 433/189 |
| 4,540,367 | 9/1985 | Sulc | 433/181 |
| 4,645,453 | 2/1987 | Niznick | 433/173 |
| 4,657,510 | 4/1987 | Gittleman | 433/173 |
| 4,713,004 | 12/1987 | Linkow et al. | 433/174 |
| 4,744,753 | 5/1988 | Ross | 433/213 |
| 4,758,160 | 7/1988 | Ismail | 433/173 |
| 4,758,161 | 7/1988 | Niznick | 433/173 |
| 4,762,492 | 8/1988 | Nagai | 433/174 |
| 4,780,080 | 10/1988 | Haris | 433/173 |
| 4,781,591 | 11/1988 | Allen | 433/174 |
| 4,790,753 | 12/1988 | Fradera | 433/174 |

FOREIGN PATENT DOCUMENTS 2812175 9/1979 Fed. Rep. of Germany ...... 433/174

OTHER PUBLICATIONS

Cat No. 196 "COC" Abutment Head for ScrewVent or MicroVent.

*Primary Examiner*—Cary E. Stone
*Attorney, Agent, or Firm*—Sprung Horn Kramer & Woods

[57] ABSTRACT

A cast dental implant abutment comprising a footpiece at the bottom end of the abutment, the footpiece having screw threads on the outer circumference thereof, and a castable cuff piece on the bottom thereof attached to the footpiece, the cuff piece on the top thereof having an indentation to accept the point of a screwdriver, the cuff piece capable of being severed at the top surface thereof at an angle other than 180°.

19 Claims, 3 Drawing Sheets

CAST DENTAL IMPLANT ABUTMENT

BACKGROUND OF THE INVENTION

1. Field of the Invention

The present invention relates to a cast dental implant abutment which provides a mating interface between internally threaded cylinder-type dental implants and various attachments or abutments to be used in fixed and removable implant prosthodontics. The threading of the inventive device permits the interchanging of the various attachments when desired by doctor and/or patient thus providing total flexibility as to retention system options over the useful life of the implant(s).

2. Background Information

Threaded systems for intra-oral implants have a built-in imperativeness when angled abutments are necessary since they can only line up properly in the jaw for prosthetic application if they are pre-tried-in at the implant site and the position subsequently replicated by custom-casting the device and its individual threading configuration. Since cylinder-type implants must also be placed where anatomically there is adequate bone quantity in the ultimate direction of the implant, angulation can be haphazard and must often be redressed if reasonable final alignment, parellelism and esthetic-phonetic standards are to be upheld. The inventive cast dental implant abutment is the first universal device to permit such a threaded system to be easily redressed. It is also possible to fabricate the inventive device within cost-effective paramaters to permit widespread utilization.

SUMMARY OF THE INVENTION

The present invention concerns cast dental implant abutment comprising a footpiece at the bottom end of the abutment, the footpiece having screw threads on the outer circumference thereof, and a castable cuff piece on the bottom thereof attached to the footpiece, the cuff piece on the top thereof having an indentation to accept the point of a screwdriver, the cuff piece capable of being severed at the top surface thereof at an angle other than 180°.

BRIEF DESCRIPTION OF THE DRAWINGS

For the purpose of illustrating the invention, there is shown in the drawings forms which may be preferred; it is understood, however, that this invention is not limited to the precise arrangements and instrumentalities depicted in the drawings.

DETAILED DESCRIPTION OF THE INVENTION

Figure 1:
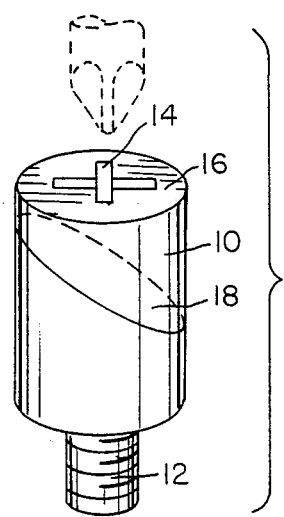
FIG. 1 is a perspective view of a cast dental implant abutment according to the present invention.

Referring to the drawings wherein like parts are designated by like reference numerals, there is depicted in FIG. 1 a cast dental implant abutment 10 according to the present invention. The abutment 10 is preferably prefabricated from an acrylic plastic. The abutment 10 has an externally threaded lower section 12 which precisely threads into the individual internal threads of a cylinder-type HA-coated implant (not shown). The inventive device is compatable with any current brand of internally-threaded, commercially available cylinder implant, as well as a superiosteal implant made with a cast-to threaded titanium cylinder as a retention abutment with interchangability options comparable to an in-the-bone cylinder implant. The acrylic abutment 10 may be either machined or injection-molded. The outer dimension of the abutment 10 corresponds to the outer dimension of the implant type it is intended to match up with, so that there will be a seamless continuity from the implant to the inventive cast abutment 10.

The top of the abutment 10 has a cross-hatch groove system 14 recessed in its surface 16 to permit screwing down the abutment 10 into the implant (not shown) in the jawbone of a patient. This is first done after the implant has integrated with the bone and been surgically uncovered. At this time the abutment 10 is screwed down into place very lightly and with a little lubricant to permit easy unscrewing without fracturing the acrylic. It is then cut off at an angle to form surface 18 to bring it into normal relationship to the other implants or abutment teeth in the arch, and also into normal relation to the opposite (opposing) arch or jaw. This redressing or redirecting of the angulation of the abutment 10 is the key to the flexibility of the abutment 10 and its univeral applicability.

Figure 2:
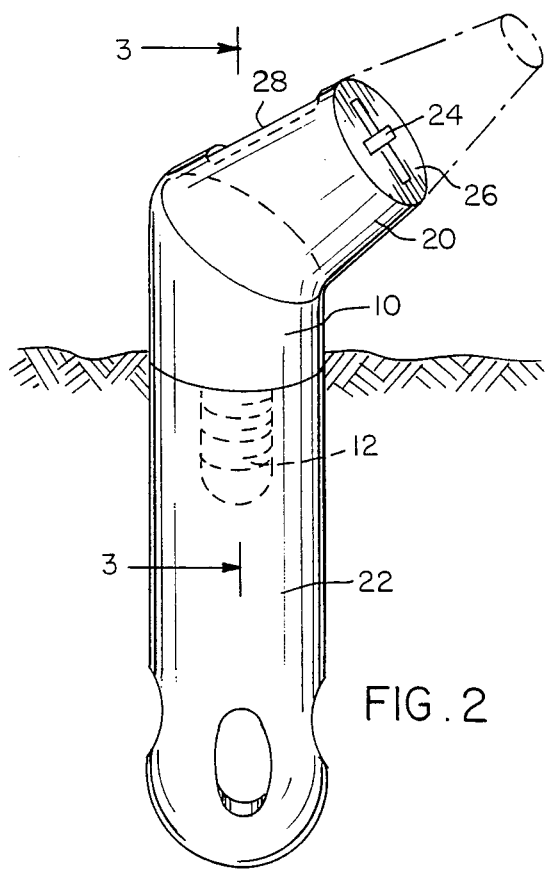
FIG. 2 is a perspective view of the cast dental implant abutment depicted in FIG. 1 with a "piggy-back" transfer coupling.
Figure 3:
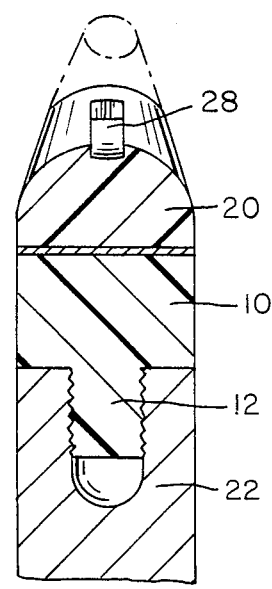
FIG. 3 is a sectional view taken along line 3—3 of FIG. 2.

There is depicted in FIG. 2 and FIG. 3 on top of the basic angled cut-off abutment 10 a "piggy-back" transfer coping 20 which is a tapered prefabricated truncated cone. This cone 20 is connected to the custom-angled first component (abutment 10) via a cold-cure acrylic or cyanoacrylate cement to provide an angled transfer coping for indirect impressioning and fabrication of the final castings, (and mating with any special retention or attachment elements, e.g., ERA-type, Magnet-type or 0-ring type). The coping 20 is preferably fabricated from an acrylic plastic. As depicted in FIG. 2, the abutment 10 with coping 20 is screwed into an implant 22. Cross-hatched recessed groove 24 on the upper surface 26 of the coping 20 permits a Phillips-type or conventional-type screwdriving of the total mated device on or off, while the keyway 28 provides a positive locking seat for the total plastic abutment combination in a polyvinyl- siloxane (or other comparable elastic material) impression. Root formers or implant analogs (not shown) are then screwed onto the plastic threaded ends of the device and then inserted into the impression, locking into the keyway groove prior to pouring the laboratory model. Final fabrication of the custom abutment is then completed on the indirect laboratory model, cast, finished, and cuff polished before the device is returned to the mouth and screwed into place.

Figure 4:
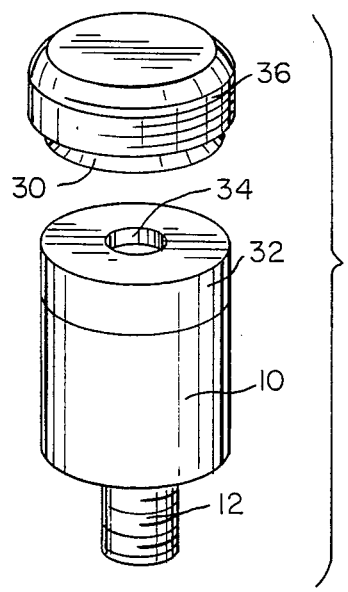
FIG. 4 is a perspective view of another cast dental implant according to the present invention with a magnetic top depicted unattached to the implant.
Figure 5:
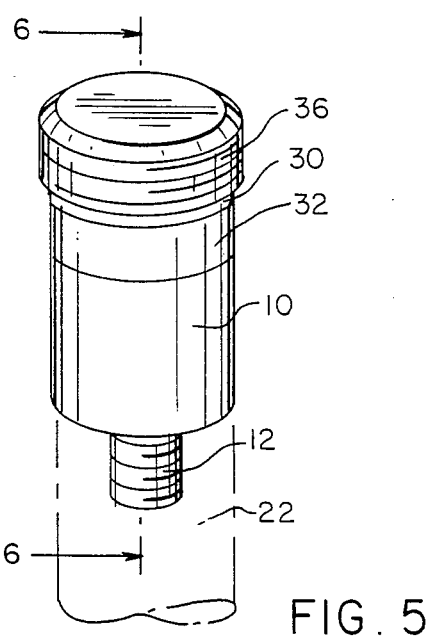
FIG. 5 is a perspective view of the cast dental implant depicted in FIG. 4 with the magnetic top disposed on top of the implant.
Figure 6:
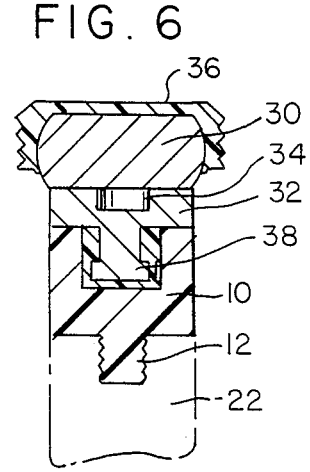
FIG. 6 is a sectional view taken along line 6—6 of FIG. 5.

FIGS. 4, 5 and 6 depict a custom-angled, screw-in abutment head for a "SHINER type" prefabricated ferro-magnetic metal keeper with a screw-down, hex-hole receptacle and with an undercut and faceted retainer foot for mechanical cast-to retention.

SHINER magnet 30 is disposed on a SHINER keeper 32 with a broached hex-hole 34 (see FIG. 4). The SHINER keeper 32 is disposed on top of abutment 10 with lower section 12 of abutment 10 screwed into implant 22. The top surface of abutment 10 could be angled as depicted in FIG. 1 (also see FIG. 9 which is discussed hereinbelow). At the bottom end of keeper 32 is faceted retainer foot 38 for attachment to abutment 10. Surrounding the top and circumference of Shiner magnet 30 is rotational housing 36.

Figure 7:
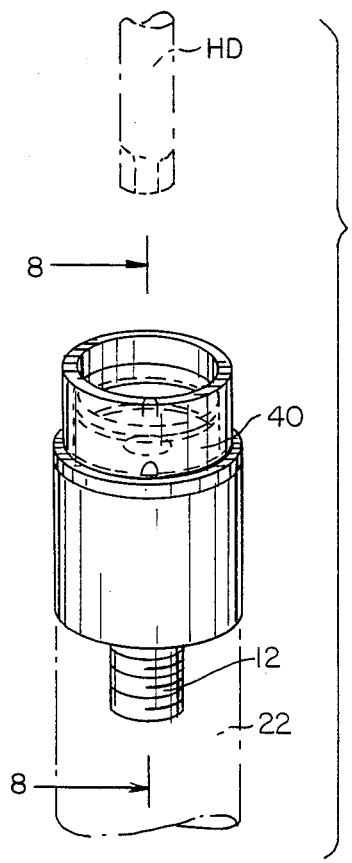
FIG. 7 is a perspective view of a female receptor component used in conjunction with the cast dental implant abutment depicted in FIG. 1.
Figure 8:
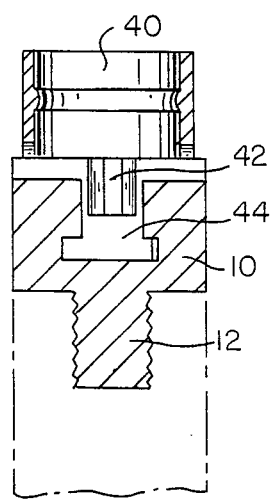
FIG. 8 is a sectional view taken along line 8—8 of FIG. 7.

In FIGS. 7 and 8 there is depicted a prefabricated, pre-hexed, machined "female" receptor component 40 for use with nylon ERA-type male attachments. Such female receptor component 40 is preferably made from titanium metal. The receptor component 40 at the bottom end thereof has an undercut and faceted retainer-foot 42 for attachment to the cuff piece of the abutment 10 (with lower section 12 screwed into implant 22). Broached hex-hole 44 permits screw-down of retainer foot 42 cast to or bonded to abutment 10, by a hex driver HD as depicted in FIG. 7, into implant 22.

Figure 9:
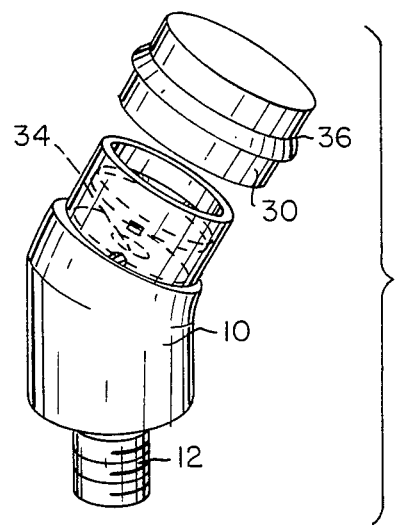
FIG. 9 is a perspective view of an angled version of the device depicted in FIGS. 4, 5 and 6.

FIG. 9 depicts an angled version of the device depicted in FIGS. 4, 5 and 6.

Thread-die (with appropriate thread-rating) is used to clean, refine and true-up threads following casting in metals of choice, namely, precious, semi-precious, non-precious or titanium (when technologically feasible).

The ideal casting goal for the present invention is to utilize cast titanium for threaded components using advanced technology Ohara casting equipment. This produces the least chance of corrosive potential at the threaded interface under intra-oral conditions. This is particularly important for the bridge abutment with permanent cemented bodies. This, however, is not possible for the SHINER ferromagnetic-steel keeper which would melt or deform at the high temperatures required for casting titanium. However, other castable metals will cast-to the SHINER keeper at lower temperatures and may be used in the present invention, or a cemented or bonded connection may be made between a custom cast titanium abutment and a ferromagnetic steel keeper or another attachment.

The present invention offers the following advantages:

(1) eliminates the unusable "sleeper" implant—all implants regardless of poor positioning are usable as abutments with this device concept;

(2) delivers a standard crown and bridge abutment if required for standard, fixed, permanently cemented bridges;

(3) eliminates screws backing-out, thread overhauling and fracturing of "retrievable" systems;

(4) expedites standard bridge trouble-shooting and redoing of damaged bridge section or segments without removing, remaking or destroying the entire bridge;

(5) avoids patient having to wear an interim removable prosthesis again while a retrievable bridge is being repaired or reworked;

(6) if a cement-in type of abutment is desired or necessary the threads may be lightly buffed away and the abutment converted to a cement-in type with minimum adjustment, again adding to its versatility—this is particularly useful when adjacent teeth or other implants are already in place with no recourse as to removal and with no room available to turn an angled, threaded abutment in the mouth.

It will be appreciated that the instant specification is set forth by way of illustration and not limitation, and that various modifications and changes may be made without departing from the spirit and scope of the present invention.

What is claimed is:

1. A plastic dental implant abutment comprising:
   a plastic footpiece at the bottom end of the implant abutment, the footpiece having screw threads on the outer circumference thereof for mating with an internally threaded implant in a jawbone of a patient,
   a plastic cuff piece, said cuff piece on the bottom therof attached to the footpiece, the cuff piece having a top surface, the cuff piece capable of being severed at the top surface thereof at an angle of other than 180°, whereby to redress the angulation of said top surface to bring the plastic implant abutment into normal relationship to other implant abutments or abutment teeth in the mouth of a patient and also into normal relationship to the opposite arch or jaw, said plastic implant abutment when cast into a metal maintaining its ability of mating with said internally threaded implant and
   an abutment selected from the group consisting of an extension and an attachment fixed to the top surface of the cuff piece,
   wherein the plastic dental implant abutment is capable of being cast into a metal.

2. A dental implant abutment according to claim 1, wherein the plastic implant abutment is fabricated from an acrylic plastic.

3. A dental implant abutment according to claim 1, wherein the cuff piece is cylindrical and has a circumference which is the same as the circumference of an implant it is to be attached to.

4. A dental implant abutment according to claim 1, wherein the extension comprises a piggy-back transfer coping, said coping attached to the top surface of the cuff piece by cementing and said coping on the top surface thereof having an indentation to accept a point of a screwdriver.

5. A dental implant abutment according to claim 4, further comprising a keyway groove disposed on a side surface of said coping and extending inwardly in the coping.

6. A dental implant abutment according to claim 4, wherein the coping is attached to the cuff piece after the top surface of the cuff piece is severed at an angle of other than 180°.

7. A dental implant abutment according to claim 4, wherein the coping is in the shape of a tapered truncated cone.

8. A dental implant abutment according to claim 1, wherein the attachment comprises a magnetic keeper having a faceted retainer foot at the bottom end thereof connected to an indentation in the top surface of the cuff piece and a magnet disposed on the top end of the keeper.

9. A dental implant abutment according to claim 8, wherein the top surface of the cuff piece is at an angle of other than 180°.

10. A dental implant abutment according to claim 8, which further comprises a rotational housing which is disposed on the magnet.

11. A dental implant abutment according to claim 1, wherein the attachment comprises a component, said component at the bottom end thereof having a faceted retainer-foot for attachment to an indentation in the cuff piece.

12. A dental implant abutment according to claim 11, wherein the component is fabricated from titanium.

13. A dental implant abutment according to claim 11, wherein the component is a female receptor component or a male component.

14. A dental implant abutment according to claim 1, wherein the attachment is selected from the group consisting of an ERA-type attachment, magnet-type attachment and O-ring type attachment.

15. A dental implant abutment according to claim 1, wherein the metal is titanium.

16. A method of forming a dental implant abutment comprising
(a) implanting an internally-threaded cylinder implant in a jawbone of a patient,
(b) after said internally-threaded cylinder implant has integrated with the jawbone of the patient, screwing a plastic dental implant abutment into said internally-threaded cylinder implant, said plastic dental implant abutment comprising:
   a plastic footpiece at the bottom end of the plastic dental implant abutment, the footpiece having screw threads on the outer circumference thereof and
   a plastic cuff piece on the bottom thereof attached to the footpiece, the cuff piece on the top surface therof having an indentation to accept the point of a screwdriver, the cuff piece capable of being severed at the top surface thereof at an angle other than 180°,
(c) severing the top surface of the plastic implant abutment at an angle other than 180°, whereby the redress the angulation of said top surface in order to bring the plastic dental implant abutment into a normal relationship with other implant abutments or abutment teeth in an arch of the mouth of the patient, and also into a normal relationship to the opposite arch or jaw of the patient,
(d) removing the plastic dental implant abutment,
(e) fixing an abutment selected from the group consisting of an extension and an attachment to the top surface of the cuff piece,
(f) casting the plastic dental implant abutment into metal and
(g) returning the resultant metal dental implant abutment to the mouth of the patient by screwing the same in place.

17. A method according to claim 16, wherein the internally-threaded cylinder implant is a cylinder-type HA-coated implant.

18. A method according to claim 16 wherein lubrication is applied to said implant abutment prior to said screwing in step (b).

19. A method according to claim 16, wherein the metal is titanium.

* * * * *